United States Patent [19]

Hornick

[11] 4,043,041
[45] Aug. 23, 1977

[54] DENTAL TREATMENT CONTROL UNIT

[76] Inventor: John Robert Hornick, 24961 Whisler Drive, El Toro, Calif. 92630

[21] Appl. No.: 683,936

[22] Filed: May 6, 1976

[51] Int. Cl.² .............................................. A61C 19/02
[52] U.S. Cl. ....................................................... 32/22
[58] Field of Search ........................... 32/22; 222/571;
141/115, 117, 119, 311 A, 116; 251/295, 5, 9, 57

[56] References Cited

U.S. PATENT DOCUMENTS

| 2,711,279 | 6/1955 | Day et al. | 141/117 |
| 3,536,294 | 10/1970 | Rodriguez | 251/295 |
| 3,759,483 | 9/1973 | Baxter | 251/5 |
| 3,986,262 | 10/1976 | Casilles | 32/22 |

Primary Examiner—Robert Peshock
Attorney, Agent, or Firm—Brown & Martin

[57] ABSTRACT

A dental treatment control unit for controlling the flow of air and/or water to dental treatment instruments. The flow of air and/or water through flexible lines to selected ones of the dental instruments is regulated by line squeezing lever arms that are normally biased for squeezing the flexible lines to prevent the flow of air and/or water therethrough. The lever arms are moved in response to the operation of a foot control mechanism to unsqueeze those air and/or water lines that are connected to the selected dental treatment instruments. A foot pedal controls a closed hydraulic system which includes a hydraulic actuator which operates a piston to move the line squeezing lever arms.

Flow of air and/or water to only selected dental treatment instruments is automatically programmed by positioning the hydraulic actuator and piston adjacent the squeezing lever arm corresponding to the selected instrument. Automatic programming is provided by a positioning lever arm having the hydraulic actuator and piston attached to one end thereof and a dental instrument receptacle attached to the other end. When a given selected dental treatment instrument is removed from the receptacle, the positioning lever arm responds by moving to position the hydraulic actuator and piston adjacent the squeezing lever arm corresponding to the given selected instrument.

11 Claims, 6 Drawing Figures

DENTAL TREATMENT CONTROL UNIT

BACKGROUND OF THE INVENTION

This invention relates to dental treatment control units for programming and regulating the supply of air and water to selected dental instruments.

Dental treatment control units of the prior art include complicated and expensive control systems for supplying air, water and vacuum to dental treatment instruments. A large number of control and regulating valves are required. In a typical unit operated by a standard pneumatic foot-controlled mechanism, the flow of air and/or water through flexible supply lines is regulated by the dentist operating valves and/or regulators in the foot-controlled mechanism. In order to vary the flow of fluid through the supply lines, regulator valves such as needle valves and air pilot valves are required in the supply lines. Such a system is complicated and expensive, and requires continuous monitoring.

Moreover, control units of the prior art include complicated mechanical, pneumatic or electrical mechanisms for programming the supply of air and/or water to selected dental treatment instruments. Such units are not able to both program and vary the amount of air and water supply in one simple operation.

SUMMARY OF THE INVENTION

The dental treatment control unit of the present invention is characterized by a regulating device which includes apparatus that are normally biased for squeezing the flexible water and/or air supply lines to prevent the flow of air and/or water therethrough, and apparatus for unsqueezing those supply lines that are connected to a selected dental treatment instrument, and by a foot-controlled mechanism which includes a closed hydraulic system including a hydraulic actuator that controls the unsqueezing apparatus in response to operation of a foot pedal. Accordingly, flow of water through the supply lines may be regulated without the use of mechanical valves in the supply lines and without the use of valves and regulators in the foot-controlled mechanism.

Another important feature of the present invention is the capability of varying the flow of air and water to the dental instruments. In most prior art control units the air and water supply lines are only controllable to be either totally on or off. In the units of this invention, the hydraulic foot-controlled mechanism may be operated to move the hydraulic actuator at varying distances thereby providing a control of the amount of air and water supplied to the dental instruments as well as turning the supply completely on or off.

In a preferred embodiment, the regulating device includes a line squeezing lever arm corresponding to each dental treatment instrument, and a post adjacent such squeezing lever arm defining a path between the post and the lever arm. The air and/or water lines for the corresponding dental treatment instrument are positioned within this path. The squeezing lever arm is normally biased to squeeze the lines between the lever arm and the post to prevent the flow of air and/or water therethrough. A piston operated by the hydraulic actuator and positionable adjacent the squeezing lever arm corresponding to the selected dental instrument, moves the lever arm to unsqueeze the lines to allow the flow of air and/or water to the selected instrument in response to operation of the foot pedal.

The present invention may further include apparatus for automatically programming the regulating device in accordance with the selection of a dental treatment instrument to enable the unsqueezing of those supply lines that are connected to the selected dental treatment instrument.

The automatic programming apparatus includes a positioning lever arm having a receptacle for a dental treatment instrument attached to one end of the arm and the piston operated by the hydraulic actuator coupled to the other end of the arm. The positioning lever arm is movable in response to removal of a given selected dental instrument from the receptacle to position the piston adjacent the squeezing lever arm corresponding to the given selected instrument. The positioning lever arm is further movable in response to replacement of the given selected instrument in the receptacle to position the piston adjacent a squeezing lever arm corresponding to a different selected dental treatment instrument.

The present invention may additionally include apparatus for preventing dripping of water from a selected dental treatment instrument following the usage thereof and the squeezing shut of the water line thereto. Such apparatus includes a pinch bulb and an additional water line. One end of the additional water line is connected to the pinch bulb and the other end is connected to the water supply line at a point between the regulating device and the dental treatment instrument. The apparatus for preventing dripping also includes a device for squeezing the pinch bulb when water flows to the dental instrument and for releasing the pinch bulb when the water supply line is squeezed shut. When the pinch bulb is released a retracting pressure is thereby provided in the water supply line to prevent water from dripping from the attached dental instrument.

The closed hydraulic control system of the present invention also may be used for controlling accessory dental treatment instruments that do not depend upon the control of the flow of air and/or water for their operation, such as hypersonic prophylaxis devices, electric drills and electrical coagulating devices. Such use of the closed hydraulic system of the present invention avoids the use of external electrical cords and controls that are common to prior art devices for controlling such accessory devices.

DESCRIPTION OF THE PREFERRED EMBODIMENT

Figure 1:
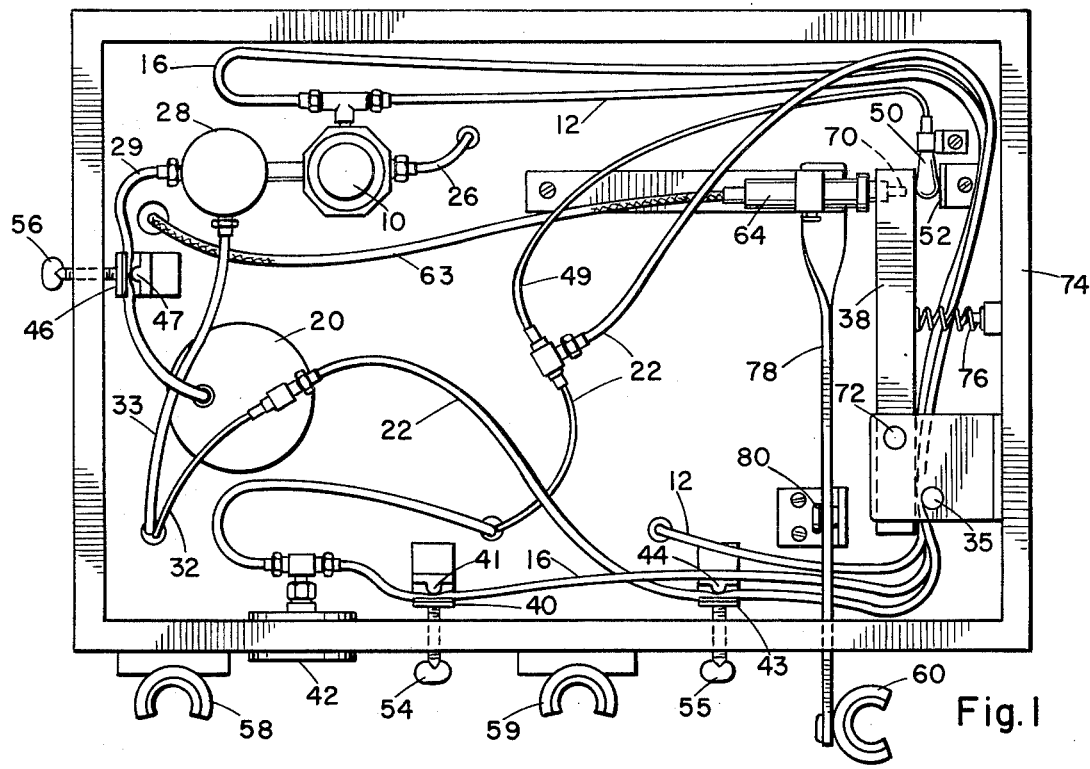
FIG. 1 is a top plan view of the preferred embodiment of the dental treatment control unit of the present invention with the cover removed.
Figure 2:
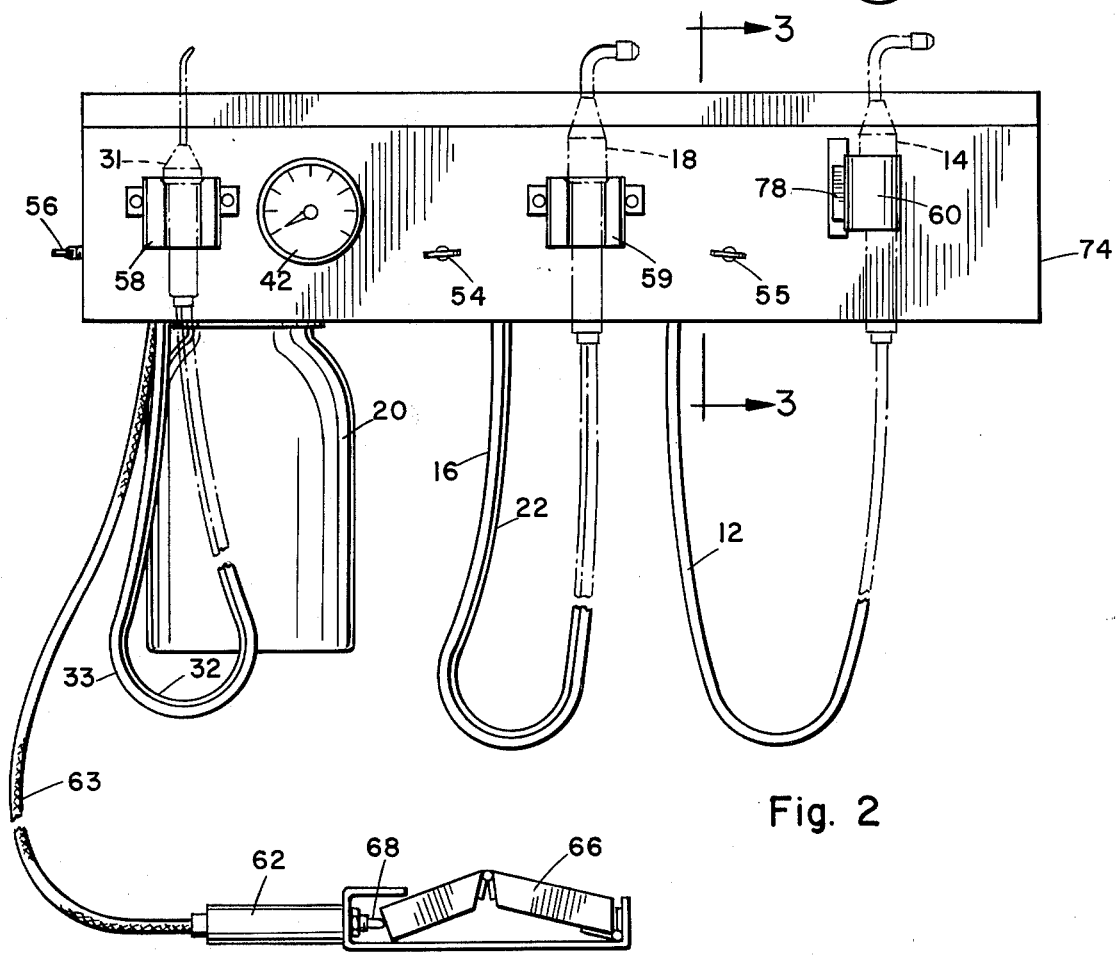
FIG. 2 is a front elevation view of the unit of FIG. 1 wherein broken lines are used to show attached dental treatment instruments.
Figure 6:
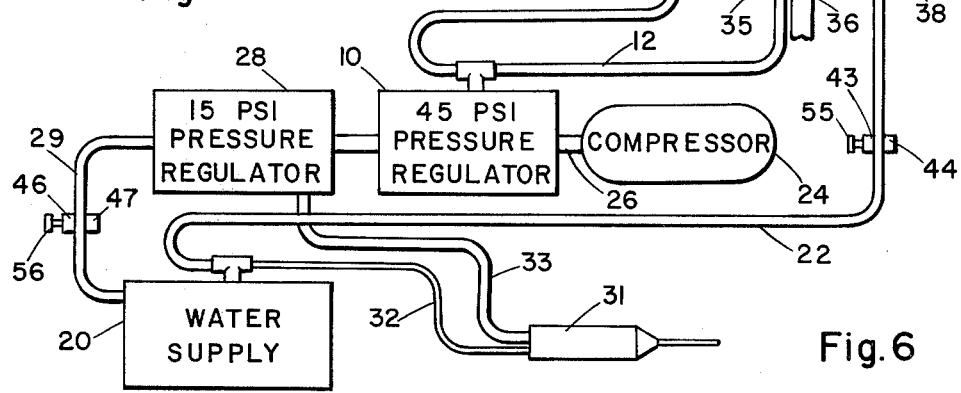
FIG. 6 is a schematic diagram showing the water and air supply system in the unit of FIG. 1.

With reference to FIGS. 1, 2 and 6, air is supplied under pressure from a 45 p.s.i. air pressure regulator 10 through an air supply line 12 to a low speed dental hand piece 14, and through an air supply line 16 to a high speed dental hand piece 18. Water is supplied under pressure from a water supply reservoir 20 through a water supply line 22 to the high speed dental hand piece 18. The supply lines 12, 16 and 22 are flexible rubber or plastic.

The 45 p.s.i. air pressure regulator 10 is supplied from an air compressor 24 through a line 26.

The water supply 20 is pressurized by air provided from a 15 p.s.i. air pressure regulator 28 through an air supply line 29. The 15 p.s.i. air pressure regulator 28 is supplied with air from the air compressor 24 through the 45 p.s.i. air regulator 10.

An air and water syringe 31 is supplied with water under pressure from the water supply reservoir 20 through a water supply line 32 and with air under pressure from the 15 p.s.i. air pressure regulator 28 through the air supply line 33.

The air supply line 12 to low speed hand piece 14 is positioned between a post 35 and a lower squeezing lever arm 36. The air supply line 16 to the high speed hand piece is positioned between the post 35 and an upper squeezing lever arm 38 and between a vernier control clamp 40 and a post 41, and passes through a pressure gauge 42. The water supply line 22 to the high speed hand piece is positioned between the post 35 and the upper squeezing lever arm 38 and between a vernier control clamp 43 and a post 44. The air line 29 from the 15 p.s.i. air pressure regulator 28 to the water supply reservoir 20 is positioned between a vernier control clamp 46 and a post 47.

Vernier control clamps 40, 43, 46 are adjusted by turning corresponding knobs 54, 55, 56 to calibrate the air and/or water pressure in the corresponding lines 16, 22, 29 positioned adjacent thereto. An additional water line 49 connects a pinch bulb 50 to the water supply line 22. The pinch bulb 50 is positioned between the upper squeezing lever arm 38 and a bar 52.

Receptacles 58, 59 and 60 are provided for receiving respectively the air/water syringe 31, the high speed hand piece 18 and the low speed hand piece 14.

A closed hydraulic system includes a hydraulic ram 62, a hydraulic line 63 and a hydraulic actuator 64. The hydraulic system is operated by a foot pedal 66. Depression of the foot pedal 66 moves a drive piston 68 into the hydraulic ram 62, which in turn causes the hydraulic actuator 64 to move a follower piston 70.

Operation of the regulating device and the programming apparatus is explained with reference to FIGS. 1, 3, 4 and 5.

The squeezing lever arms 36, 38 are pivotally mounted on a pin 72 and also are mounted on the housing 74 by springs 75 and 76. The springs 75 and 76 normally bias the squeezing lever arms 36, 38 in a position wherein they clamp the lines 12, 16 and 22 against the post 35 to squeeze them shut.

When the follower piston 70 moves in response to depression of the foot pedal 66, it presses against whichever squeezing lever arm 36 or 38 that it 70 is then positioned adjacent thereto and causes the respective arm 36 or 38 to move to unsqueeze the respective lines 14 or 16 and 22 that are clamped against the post 35 by that particular lever arm 36 or 38, thereby allowing air and/or water to flow through the lines 14 or 16 and 22 to the respective dental handpieces 14 or 18.

The programming apparatus includes a positioning lever arm 78, which is pivotally mounted on a pin 80. The hydraulic actuator 64 is attached to one end of the lever arm 78, and the receptacle 60 for the low speed hand piece 14 is attached to the other end. When the low speed hand piece 14 is removed from the receptacle 60, the positioning lever arm 78 moves to the position shown by the broken lines in FIG. 3, wherein the hydraulic actuator 64 and follower piston 70 are positioned adjacent the lower squeezing lever arm 36. Depression of the foot pedal 66 then will allow air to flow through line 12 to the low speed hand piece 14.

Figure 3:
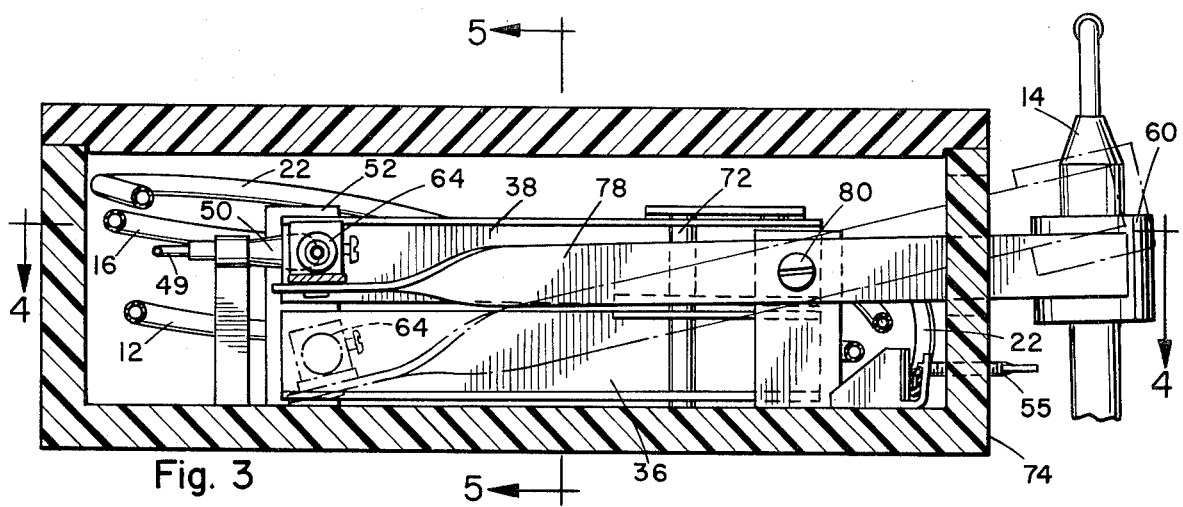
FIG. 3 is an enlarged sectional view taken on line 3—3 of FIG. 2, wherein broken lines are used to show the positioning lever arm in the position to which it moves when a given selected dental instrument is moved from its receptacle.
Figure 4:
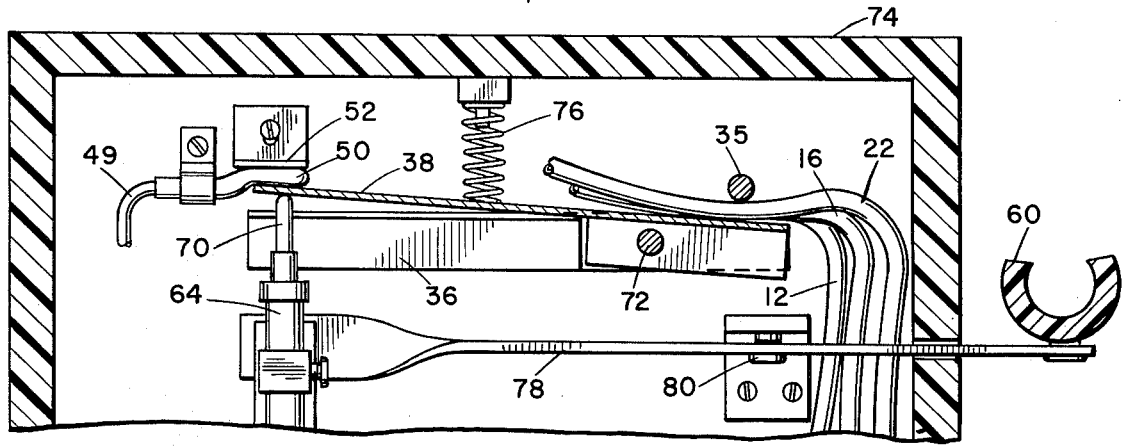
FIG. 4 is a partial sectional view taken on line 4—4 of FIG. 3.
Figure 5:
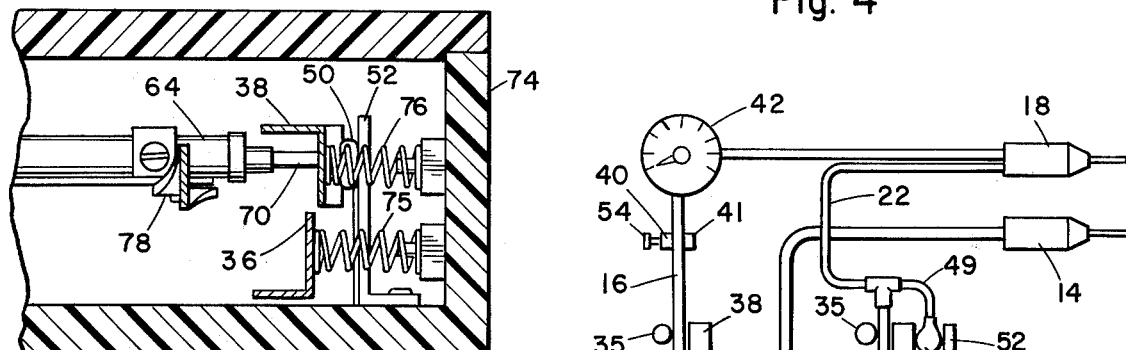
FIG. 5 is a partial sectional view taken on line 5—5 of FIG. 3.

When the low speed hand piece 14 is returned to the receptacle 60 the positioning lever arm 78 returns to the position shown by the solid lines in FIG. 3 and as shown in FIGS. 4 and 5, wherein the hydraulic actuator 64 and follower piston 70 are positioned adjacent the upper squeezing lever arm 38 which clamps the supply lines 16 and 22 for the high speed hand piece 18. When the high speed hand piece 18 is removed from its receptacle 59, the positioning lever arm 78 remains in this last mentioned position, and depression of the foot pedal 66 allows air and water to flow through lines 16 and 22 to the high speed hand piece 18.

It is readily seen in FIGS. 4 and 5 that when the upper squeezing lever arm 38 is moved to unsqueeze the lines 16 and 22 in order to allow air and water to flow therethrough that the pinch bulb 50 is squeezed by the lever arm 38 against the bar 52. When the lever arm is allowed to return to its normally biased position, as shown in FIG. 1, the pinch bulb 50 is released and thereby creates a retracting pressure in the water line 49 which in turn sucks water in from the line 22 from the hand piece 18 in order to prevent dripping of water therefrom after it 18 has been used and the dentist has removed pressure from the foot pedal 66. The pinch bulb 50 replaces expensive air piloted and electrical valve mechanisms in prior art devices.

While the invention has been illustrated by a specific embodiment, the invention is not limited to the specific arrangement of components in the housing 74 or the arrangement of the dental treatment instruments as shown. It would be well within the spirit of the invention to provide a different arrangement of dental instruments. As many instruments as desired could be operated by the simple control unit of the present invention. An additional number of supply lines and corresponding squeeze bars and pinch bulbs also could be utilized.

Having described my invention, I now claim:

1. A dental treatment control unit for controlling the flow of air and water to dental treatment instruments, comprising,
    flexible lines for supplying air and/or water to said instruments,
    means for regulating the flow of air and/or water in said lines to selected ones of said instruments, and
    foot-controlled means for controlling said regulating means
    characterized by
    said regulating means comprising
        means that are normally biased for squeezing said flexible lines to prevent the flow of air and/or water therethrough, and means for unsqueezing those of said lines that are connected to a selected dental treatment instrument; and said foot-controlled means comprising
  a closed hydraulic system including a hydraulic actuator that controls said unsqueezing means in response to operation of a foot pedal.

2. A dental treatment control unit according to claim 1, wherein the regulating means comprise
  a line squeezing lever arm corresponding to each dental treatment instrument,
  a post adjacent said squeezing lever arm defining a path between the post and said lever arm within which path the air and/or water lines for said corresponding dental treatment instrument are positioned, wherein said lever arm is normally biased to squeeze the lines between said lever arm and the post to prevent the flow of air and/or water therethrough, and
  a piston operated by the hydraulic actuator and positionable adjacent said squeezing lever arm corresponding to said selected dental treatment instrument to move said lever arm to unsqueeze said lines to allow the flow of air and/or water to said selected instrument in reponse to operation of said foot pedal.

3. A dental treatment control unit according to claim 2, further comprising means for automatically programming the positioning of the piston adjacent the squeezing lever arm corresponding to said selected dental treatment instrument, comprising,
  a positioning lever arm having a receptacle for a dental treatment instrument attached to one end of said arm and said piston coupled to the other end of said arm, wherein the positioning lever arm is movable in response to removal of a given selected dental treatment instrument from the receptacle to position the piston adjacent said squeezing lever arm corresponding to said given selected instrument.

4. A dental treatment control unit according to claim 3, wherein the positioning lever arm is further movable in response to replacement of said given selected instrument in said receptacle to position the piston adjacent a squeezing lever arm corresponding to different selected dental treatment instrument.

5. A dental treatment control unit according to claim 1, further comprising,
  means for automatically programming the regulating means in accordance with the selection of a said dental treatment instrument to enable the unsqueezing of those lines that are connected to said selected dental treatment instrument.

6. A dental treatment control unit according to claim 5, wherein the regulating means comprise
  a line squeezing lever arm corresponding to each treatment instrument,
  a post adjacent said squeezing lever arm defining a path between the post and said lever arm within which path the air and/or water lines for said corresponding dental treatment instrument are positioned, wherein said lever arm is normally biased to squeeze the lines between said lever arm and the post to prevent the flow of air and/or water therethrough, and
  a piston operated by the hydraulic actuator and positionable adjacent said squeezing lever arm corresponding to said selected dental treatment instrument to move said lever arm to unsqueeze said lines to allow the flow of air and/or water to said selected instrument in reponse to operation of said foot pedal;

and the programming means comprise
  a positioning lever arm having a receptacle for a dental treatment instrument attached to one end of said arm and said piston coupled to the other end of said arm, wherein the positioning lever arm is movable in response to removal of a given selected dental treatment instrument from the receptacle to position the piston adjacent said squeezing lever arm corresponding to said given selected instrument and is further movable in response to replacement of said given selected instrument in said receptacle to position the piston adjacent a squeezing lever arm corresponding to a different selected dental treatment instrument.

7. A dental treatment control unit according to claim 1, further comprising,
  means for preventing dripping of water from a selected dental treatment instrument following the usage thereof and the squeezing shut of the water supply line thereto.

8. A dental treatment control unit according to claim 7, wherein the dripping preventing means comprise,
  a pinch bulb corresponding to said selected dental instrument,
  an additional water line having one end connected to the water supply line at a point between the regulating means and said dental instrument and having the other end connected to the pinch bulb; and
  means for squeezing the pinch bulb when the regulating means are controlled to allow water to flow through the water supply line to said instrument, and for releasing the pinch bulb when the regulating means are controlled to squeeze shut the water supply line, thereby causing the pinch bulb to provide a retracting pressure in the water supply line when the water supply line is squeeze shut.

9. A dental treatment control unit according to claim 8, wherein the regulating means comprise
  a line squeezing lever arm corresponding to each dental treatment instrument,
  a post adjacent said squeezing lever arm defining a path between the post and said lever arm within which path the air and/or water lines for said corresponding dental treatment instrument are positioned, wherein said lever arm is normally biased to squeeze the lines between said lever arm and the post to prevent the flow of air and/or water therethrough, and
  a piston operated by the hydraulic actuator and positionable adjacent said squeezing lever arm corresponding to said selected dental treatment instrument to move said lever arm to unsqueeze said lines to allow the flow of air and/or water to said selected instrument in response to operation of said foot pedal; and
the means for squeezing the pinch bulb comprise
  a bar adjacent each squeezing lever arm corresponding to a dental instrument having a water supply line thereto, said bar defining an opening between said lever arm and said bar within which opening said corresponding pinch bulb in positioned so as to be squeezed when said squeezing lever arm is moved to unsqueeze said water supply line, and so as to be released when said squeezing lever arm is moved to squeeze said water supply line shut.

10. A dental treatment control unit according to claim 1, for additionally controlling accessory dental treatment instruments that are not dependent upon controlling the flow of air and/or water thereto, further comprising,
  means for controlling said accessory instruments in response to the operation of said hydraulic actuator.

11. A dental treatment control unit for controlling the flow of air and water to dental treatment instruments, comprising,
  flexible lines for supplying air and/or water to said instruments,
  means for regulating the flow of air and/or water in said lines to selected ones of said instruments, and
  foot-controlled means for controlling said regulating means
characterized by
said regulating means comprising
  means that are normally biased for squeezing said flexible lines to prevent the flow of air and/or water threrethrough, and means for unsqueezing those of said lines that are connected to a selected dental treatment instrument; and
said foot-controlled means comprising
  a closed system including an actuator that controls said unsqueezing means in response to operation of a foot pedal.

* * * * *